United States Patent [19]

Friedman et al.

[11] Patent Number: 5,449,611
[45] Date of Patent: Sep. 12, 1995

[54] POLYAROMATIC HYDROCARBON (PAH) IMMUNOASSAY METHOD, ITS COMPONENTS AND A KIT FOR USE IN PERFORMING THE SAME

[75] Inventors: Stephen B. Friedman, Chapel Hill; Randy L. Allen, Apex, both of N.C.

[73] Assignee: Ensys, Inc., Research Triangle Park, N.C.

[21] Appl. No.: 97,223

[22] Filed: Jul. 27, 1993

[51] Int. Cl.$^6$ .................... G01N 33/577; C07K 16/44
[52] U.S. Cl. .................................. 435/7.93; 435/188; 436/815; 530/388.9
[58] Field of Search .................... 435/172.2, 188, 7.93; 530/388.9; 935/110

[56] References Cited

U.S. PATENT DOCUMENTS 5,145,790  9/1992  Mattingly et al. .................. 436/536

FOREIGN PATENT DOCUMENTS

WO88/09798  12/1988  WIPO .

OTHER PUBLICATIONS

Chemical Abstracts, CA 120:297406f, "PAH RIS Soil Test—A Rapid, On-Site Screening Test for Polymuclear Aromatic Hydrocarbons in Soil", McDonald et al., J. AOAC Inc. 1994, 77(2), 466–72.
Journal of Soil Contamination, 1(3): 227–237 (1992), "A Rapid and Sensitive Immunoassay for the Detection of Gasoline and Diesel Fuel in Comtaminated Soil", Allen et al.
Environmental Technology, vol. 23, pp. 1027–1035, "Development and Applications of an Ultrasensitive Quantitative Enzyme Immuno–Assay for Benzo(a)pyrene in Environmental Samples", (1991) Bacigalupo et al.
PCT/US94/12218, PCT International Search Report, date mailed Feb. 17, 1995.
M. Gomes et al, Chem. Res. Toxicol., vol. 3, pp. 307–310 (1990).
G. Wisdom, Clinical Chemistry, vol. 22, No. 8, pp. 1243–1255 (1976).
M. O'Sullivan et al., Annals of Clinical Biochemistry, vol. 16, pp. 221–232.

*Primary Examiner*—Mary E. Ceperley
*Attorney, Agent, or Firm*—Oblon, Spivak, McClelland, Maier, & Neustadt

[57] ABSTRACT

An immunoassay method that integrates a sample processing component that enables the testing of a variety of environmental matrixes and the components for performing the method, wherein the immunoassay utilizes a monoclonal anti-PAH antibody to detect the presence or absence of PAH contamination in a sample when tested in a field or laboratory location.

22 Claims, 1 Drawing Sheet

FIG. 1

POLYAROMATIC HYDROCARBON (PAH) IMMUNOASSAY METHOD, ITS COMPONENTS AND A KIT FOR USE IN PERFORMING THE SAME

BACKGROUND OF THE INVENTION

1. Field of the Invention

The present invention relates to methods, compositions and kits for performing polyaromatic hydrocarbon (PAH) immunoassays.

2. Discussion of the Background

Testing is an essential, and integral, component of all environmental protection and restoration activities. It is the rate limiting element that influences the time, cost, and overall efficiency of project management.

The Environmental Protection Agency (EPA) has long promoted and supported the concept of screening methods to supplement laboratory analysis and increase overall efficiency. The need for more effective methods has been recognized in the Superfund Amendments and Reauthorization Act of 1986 which specifies the development and evaluation of alternative time and cost-saving methods that will assist in the eventual remediation of the nations Superfund sites.

Effective field screening methods can increase the efficiency of site management and improve overall data quality when used to supplement the services of regional laboratories. The development of these methods, however, requires a technology that will be compatible with numerous compounds and matrixes and yet be simple, effective and rugged enough to be incorporated into a protocol for use in the field.

Screening methods need to provide fast, simple, cost-effective and reliable information when operated under field conditions. The reagents and equipment should be portable and stable at ambient conditions, and the claims relating to performance should accurately reflect anticipated field use. The methods should be able to rapidly provide an ample quantity of data, and the protocol should be simple to perform and safe to use. Performance characteristics relative to sensitivity, freedom from matrix interferences and cross-reacting compounds, and correlation to an acceptable reference method should be carefully evaluated. Developers must maintain high, and consistent, quality standards relative to the consistency of their manufacturing protocols, the adequacy of in-process and pre-release quality control methods, and the reliability of their product claims. A necessary characteristic of particular significance for screening methods, is that they exhibit a very low frequency of false negative results.

Screening methods detect contamination at specified concentrations. The concentration may relate to a hazardous threshold, a clean-up target, or a process-control parameter. The potential implications of false negative data far outweigh those of false positive results. The consequence of a false positive, while a costly problem that needs to be minimized, results in additional testing or treatment. False negative data, however, provides an erroneous perception of a clean site, and may have serious environmental and legal consequences. Safeguards that minimize the incidence of false negative results are imperative. Appropriate control over the frequency of false positive data needs to be established and maintained.

Contamination of soil with polyaromatic hydrocarbons (PAH) is a serious problem at manufactured gas plant sites, coking operations, wood preserving operations that have used creosote as a wood preservative, and petrochemical plant waste disposal sites. The federal and state regulatory agencies are mandating the clean-up of many of these sites due to the carcinogenic nature of some of the PAHs.

Polyaromatic hydrocarbons (PAHs), or polynuclear aromatic compounds (PNAs), are fused ring aromatic compounds classified by the number of carbon rings. Sixteen of these PAHs are listed as hazardous compounds by the EPA (see Table I below).

TABLE I

| Listed PAH Compounds | |
|---|---|
| acenaphthene | acenaphthylene |
| anthracene | benzo[a]anthracene |
| benzo[a]pyrene | benzo[b]fluoranthene |
| benzo[g,h,i]perylene | benzo[k]fluoranthene |
| chrysene | dibenzo[a,h]anthracene |
| fluoranthene | fluorene |
| indeno[1,2,3-cd]pyrene | naphthalene |
| phenanthrene | pyrene |

They are further divided into carcinogenic and non-carcinogenic PAHs. The two and three ring PAHs are non-carcinogenic, while several of the four, five and six ring PAHs are carcinogenic. The four ring PAHs, chrysene and benzo[a]anthracene, the five ring PAHs, benzo[a]pyrene, benzo[b]fluoranthene, benzo[k]fluoranthene, and dibenzo[a,h]anthracene, and the six ring PAH, indeno[1,2,3-cd]pyrene, are listed as carcinogenic PAHs with benzo[a]pyrene being the most potent carcinogen among the PAHs. Regulatory concern is generally focused on benzo[a]pyrene, total carcinogenic PAHs, and total PAHs.

The laboratory methods usually employed for PAH analysis, EPA methods 8270 (GC/MS) and 8310 (HPLC), are relatively expensive, typically $200–500, and suffer from the same laboratory turnaround time requirements (2–4 weeks) as other lab methods. While the minimum detection levels for these methods can be quite low (10–1500 ppb), PAH containing samples are usually quite "dirty", routinely resulting in much higher levels of practical quantitation, typically on the order of 1–100 ppm. Due to the complicated chemical nature of coal tar or petroleum residues, PAHs are difficult to analyze accurately using the conventional methods. Although the results obtained using the standard EPA methods do not show gross differences between labs, serious discrepancies are seen with the carcinogenic PAHs when they occur at high concentrations.

Immunoassay methods combine the specific binding characteristics of an antibody molecule with a read-out system that is used to detect and quantify compounds. Current immunoassay technology benefits from the diversity of detection systems developed that use enzyme-catalyzed chromogenic reactions, radionuclides, chemiluminescence, fluorescence, fluorescence polarization and a variety of potentiometric and optical biosensor techniques. Improvements in the sensitivity achieved has necessitated the generation of new descriptive nomenclature for methods that can now detect "zeptomolar" ($10^{-21}$, 600 molecules) concentrations.

The U.S. Environmental Protection Agency has concluded that immunoassay technology provides an advantage over the traditional analytical methods (gas chromatography (GC), gas chromatography/mass spectrometry (GC/MS), high performance liquid chromatography (HPLC) by increasing the sample throughput at a lower cost (Van Emon et al. in *Field Screening methods for Hazardous Wastes and Toxic Chemicals*, p. 815-818 (1991)). The EPA SW-846 Organic Methods Work Group have approved draft immunoassay methods for inclusion into the next revision of the SW-846 methods. From this information it is obvious that newly developed reagents and immunoassays are becoming acceptable analytical tools for the environmental field.

While various immunoassay methods have been described which target specific individual PAH compounds, these methods require coupling the PAH compound to a DNA fragment (see Harris, U.S. Pat. No. 4,794,074 and Wallin et al Cancer Lett., 22(2), 163-70 (1984)), using a monoclonal antibody for analysis of only a single PAH compound in a single test (see Dougherty, E. P. 0,242,589) or using a monoclonal antibody to detect specifically benzo(a)pyrene and its metabolites in urine or water (see Roda et al, *Environ. Technol.*, 12(11), 1027-35 (1991 and Gomes et al, *Chem. Res. Toxicol.*, 3(4), 307-10 (1990).) However, no immunoassay methods are available for the detection of PAHs in a variety of matrices of various origin and overall compositions.

Thus, an immunoassay method is needed which will provide reliable accurate and fast results in the field for PAH contaminants, regardless of origin or exact composition. Such an assay would increase the efficiency of environmental site management activities such as characterization (mapping), remediation monitoring, and regulatory compliance.

SUMMARY OF THE INVENTION

Accordingly, one object of the present invention is to provide a PAH immunoassay method which is field compatible, fast and accurate.

A further object of the present invention is to provide a PAH immunoassay method which gives minimal false negative results.

Another object of the present invention is to provide a PAH immunoassay method which detects PAH contamination derived from a wide variety of unknown sources about equivalently, where such method is independent of the detection of a single compound in the sample, since concentrations of single compounds vary between samples and locations.

Another object of the present invention is to provide a PAH immunoassay which is simple to perform and easy to interpret in a field or laboratory setting by operators inexperienced in the art.

Another object of the present invention is to provide an anti-PAH monoclonal (MAb) antibody which is useful in the above-mentioned PAH immunoassay.

Another object of the present invention is to provide an anti-PAH monoclonal antibody with specific reactivity towards a characteristic plurality of compounds found in PAH contaminated samples, namely the 3-4 ring PAHs and at least some of the 5-6 ring PAHs, with preferential recognition for the more prevalent 3 ring phenanthrene.

Another object of the present invention is to provide a reagent (e.g., an enzyme conjugate reagent) for use with the monoclonal antibody in competitive binding type immunoassays.

Another object of the present invention is to provide immunogens which elicit an anti-PAH monoclonal antibody response.

Another object of the present invention is to provide a kit for performing a PAH immunoassay on various sample matrices.

Another object of the present invention is to provide a sample processing procedure for preparing samples from various matrices for use in the immunoassay of the present invention.

These and other objects of the present invention, which will become apparent from a reading of the description of the invention given hereinbelow, have been found by the inventors to be satisfied by their discovery of a monoclonal antibody which recognizes a characteristic plurality of compounds common to a variety of PAH contaminants and to the inventors' discovery of immunogens which can be used to generate such a monoclonal antibody.

PAH contaminated samples of different sources, differ from each other with regard to the nature of the PAH compounds present. However, most (>85%) contain phenanthrene in addition to a plurality of other PAH compounds, although the relative amounts of each individual compound in this plurality may vary from one PAH contaminated site to another. The antibody of the present invention recognizes this plurality of compounds, primarily phenanthrene, which is a common and prevalent PAH contaminant, and others with relative equivalency, and can therefore be used to detect the presence of PAH contamination in a sample.

The present invention accordingly provides, among its varied embodiments, both an antibody and a test kit which incorporates the antibody. The kit is useful to detect the presence of PAH contamination in a sample because the antibody exhibits approximately equivalent detection of PAH compounds and preferentially detects phenanthrene, regardless of origin or diversity of chemical composition, and thereby provides an easy-to-use and highly reliable kit for environmental PAH testing applications.

BRIEF DESCRIPTION OF THE FIGURES

A more complete appreciation of the present invention and many of the attendant advantages thereof will be readily obtained as the same becomes better understood by reference to the following detailed description when considered in connection with the accompanying figures, wherein.

DETAILED DESCRIPTION OF THE PREFERRED EMBODIMENTS

In one embodiment, the present invention provides an immunoassay for determining the presence of PAH contamination in a sample (suspected to contain PAH). The immunoassay comprises:

(i) contacting a monoclonal antibody with specific reactivity towards a characteristic plurality of PAH compounds found in contaminated samples, with preferential recognition of the phenanthrene component, with a mixture of the sample and a reagent which is cross reactive with the monoclonal antibody, to form an assay mixture;

(ii) incubating the assay mixture to allow competitive binding to the antibody between at least one member of the characteristic plurality of compounds from the PAH contaminant, if present, in the sample and the reagent to form a monoclonal antibody complex; and (iii) detecting the extent of binding of the reagent to the monoclonal antibody and correlating the amount of bound reagent to the amount of PAH contaminant in the sample.

In another embodiment, the invention provides an immunoassay kit which comprises three basic components: (1) a monoclonal antibody with specific reactivity towards a characteristic plurality of PAH compounds (2) a reagent cross reactive with the monoclonal antibody and susceptible to detection, and optionally (3) a signal-generating reagent.

To induce, in a vertebrate host, the formation of the present monoclonal antibodies that can be used to detect the characteristic plurality of PAH compounds, an immunogen is used which contains a derivative moiety which mimics the structural features of the prevalent phenanthrene and a characteristic plurality of other PAH compounds. The immunogen is synthesized, by standard methods, by coupling a derivative moiety to an immunologic carrier molecule.

Examples of suitable methods for coupling a derivative moiety to an immunologic carrier molecule have been described in co-pending U.S. application Ser. Nos. 07/984,098 and 08/068,093 to Friedman et al, which are hereby incorporated by reference.

Known immunological carrier moieties can be used, including albumin (e.g., bovine serum albumin), thyroglobulin (e.g., bovine thyroglobulin), hemocyanin (e.g., keyhole limpet hemocyanin), polyamino acids and other molecules having a minimum size, complexity, and foreignness to the host animal. Carriers are usually of the class of proteins, polypeptides or peptides having a molecular weight of at least 1,000 daltons and preferably >10,000 daltons. Carrier molecules may have a reactive group(s) available for covalent conjugation of the derivative. R-groups (e.g., COOH, $NH_2$) of amino acids or sugar moieties of glycoproteins are often used for this purpose in the synthesis of immunogens.

Preferably, the immunogen is a compound of the formula wherein Ar is an aromatic benzenoid hydrocarbon group having from 2 to 4 benzenoid rings, each ring of which may be substituted by one or more substituents selected from the group consisting of H, $CH_3$ and $CH_2CH_3$; X and Y are each, independently or X is —COO—, or a single bond wherein $R^1$ is selected from the group consisting of H, $C_1$-$C_2$ alkyls, and linear, branched and cyclic $C_3$-$C_6$ alkyls; n is 0 or an integer from 1 to 4 where Z is an immunologic carrier molecule and the rest of the molecule is the derivative moiety of the immunogen. Preferably one or two of the substituents on the Ar group is methyl. A most preferred immunogen is wherein $R^2$ to $R^8$ are each independently a member selected from the group consisting of H, $CH_3$, and $CH_2CH_3$ and Z is an immunologic carrier molecule.

Small environmental chemicals, such as naphthalene and phenanthrene, by themselves are too small to stimulate an immune response and elicit an antibody response. To elicit an antibody response, derivatives of small molecules, such as naphthalene, are attached through a chemical bridge to a much larger "carrier" molecule prior to immunization. According to the invention, the small molecules and accompanying bridge structures of the derivative are designed so that they mimic immunologically at least one common feature present in the defined molecular pool of interest. A number of modifications to the bridge structure (X—$(CH_2)_n$—Y) are possible and produce similar results. Any vertebrate is a suitable host for the immunization procedure, such as mice, rats, dogs, pigs and other domestic animals, with mice being preferred. Alternatively, in vitro immunization may be used.

The immunoassay method of the present invention uses a hybridoma-derived monoclonal antibody. The monoclonal antibody is selected using a multi-parameter screening process. A reactive panel profiling system is developed to identify appropriate cell lines and monoclonal antibodies on the basis of sensitivity, PAH recognition characteristics, and freedom of interference from confirmed negative soil samples or cross-reacting compounds. The monoclonal antibody binds selectively to a defined pool of molecules present in PAH contaminants and preferably to phenanthrene and anthracene. The antibody allows the method to rapidly detect PAH contamination, regardless of origin, at, or above, a concentration of 1 ppm in soil at a ≧95% confidence level, with lower concentrations detectable at lower confidence levels, because most samples contain phenanthrene and because of the cumulative concentration of other PAH compounds. The antibody operates through the selective recognition of specific polycyclic aromatic compounds.

The reporter molecule reagent of the present invention, which in a preferred embodiment is an enzyme conjugate reagent, is cross reactive with the monoclonal antibody and capable of providing a detectable signal, either alone or in combination with one or more co-reagents. Preferably, the reporter molecule reagent comprises a compound of formula wherein Ar is an aromatic benzenoid hydrocarbon group having from 2 to 6 benzenoid rings, each ring of which may be substituted by one or more substituents selected from the group consisting of H, CH₃ and CH₂CH₃; X and Y are each, independently or X is

—COO—, or a single bond wherein $R^9$ is selected from the group consisting of H, $C_1$-$C_2$ alkyls, and linear, branched and cyclic $C_3$-$C_6$ alkyls; and n is 0 or an integer from 1 to 4.

The reporter moeity used in the present invention may include an enzyme, a fluorescent compound, a chemiluminescent compound, a bioluminescent compound, a dyed latex particle or a radioactive atom. A preferred reporter moiety for use in the enzyme-conjugate reagent of the present invention includes an enzyme selected from the group consisting of horseradish peroxidase, alkaline phosphatase, glucose oxidase, β-galactosidase, glucose oxidase, G6-PDH (glucose-6-phosphate dehydrogenase) or urease, with horseradish peroxidase being most preferred.

A most preferred enzyme conjugate reagent is a compound of formula wherein $R^{10}$ to $R^{17}$ are each independantly selected from the group consisting of H, CH₃, and CH₂CH₃, and HRP represents horseradish peroxidase.

The enzyme conjugate is prepared using conventional methods such as those described in U.S. applications Ser. Nos. 07/984,098 and 08/068,093 to Friedman et al.

The enzyme conjugate of the present invention must be cross-reactive with the anti-PAH antibody of the present invention and capable of inducing a detectable change in the sample by reaction with a signal producing substrate or reagent used in the immunoassay.

The immunoassay-based system of the present invention uses a signal producing reagent which, upon reaction with the bound enzyme conjugate/antibody complex after incubation, provides a detectable signal indicating the presence or absence of PAH contamination in the sample being tested. Suitable signal producing reagents include a hydrogen peroxide/tetramethyl benzidine pair, or a phenylene diamino, in combination with an enzyme conjugate reagent containing horseradish peroxidase, o-nitrophenyl-β-D-galactopyranoside (ONPG) in combination with an enzyme conjugate reagent containing β-galactosidase, o-nitrophenylphosphate in combination with an enzyme conjugate reagent containing alkaline phosphatase, or glucose in combination with glucose oxidase or G6-PDH. The method of the present invention preferably uses the combination of a hydrogen peroxide (H₂O₂) substrate solution with a tetramethylbenzidine (TMB) chromogen, with the combination producing a blue chromophore upon oxidation of TMB by H₂O₂.

An important characteristic of the immunoassay of the present invention, as well as with any field screening method, is the minimization of false negative results without producing excessive false positive data. Statistically, therefore, the standard concentration should not be set at the concentration of interest, but below it. Setting the standard concentration to coincide with the regulatory concentration would result in a 50% false negative incidence. To minimize this effect, standards used in the immunoassay of the present invention should be offset in concentration to produce a >95% confidence level of detecting contamination at, or above, the desired level. For example, to obtain a method which gives results having a >95% confidence level for detection of PAHs at 1 ppm, a 0.65 ppm standard could be used. The standard is set below the target level. The actual concentration of standard used is a function of the binding characteristics of the assay and the overall precision of the method.

Immunoassay methods have conventionally been used to test liquid matrixes such as blood, urine, and water. This method is designed to test also solid matrices. However, the testing of solid matrices requires that the issues of sample collection, dispersion, extraction and clarification be addressed and integrated with the immunoassay component. While the assay of the present invention may be performed on samples of a wide range of qualities, a reproducible, particulate-free, leachate is preferred for optimum results. The extraction and recovery of a compound from soil requires the selection of an appropriate solvent system, adequate sample dispersion, sufficient time for partitioning, non-invasive clarification and compatibility with the subsequent immunochemistry. Current sample processing for analytical detection methods limits the efficiency of these methods and is slow and expensive.

One suitable method for sample preparation involves the gravimetric collection of a 10 g sample using a small battery-operated balance. The sample is then transferred into a dispersion vial containing methanol and conventional dispersing pellets, and is subjected to a one minute manual agitation for adequate dispersion and partitioning of the analyte into the solvent. Filtration of the sample suspension to produce a particulate-free extract can be accomplished using a fingertip-operated filter unit fitted with non-adsorbing filters. The clarified leachate is then ready for testing with the immunoassay of the present invention following dilution or otherwise removal of the solvent. Solvent-resistant antibody reagents could be used to eliminate or limit the need for the solvent dilution step.

Buffers, detergents (e.g. Tweens, Tritons, etc.) or solvents, used alone, or in combination, have proven to be effective for extraction. Analytical methods for the analysis of solid waste rely upon gravimetrically collected samples, and results are reported in gravimetric units. Volumetric sampling for solid waste should preferably be avoided because of the potential bias that may be caused by the specific gravity of the sample.

The present immunoassay method permits the simultaneous testing of soil samples to detect contamination at multiple concentrations and to facilitate the construction of contamination contour profiles. The method is preferably for screening purposes and several safeguards have been incorporated to minimize the incidence of false negative results.

The basic characteristics of specificity and equivalent detection of the assay of the present invention are a result of the monoclonal antibody (MAb) and the reagent. The assay provides approximately equal recognition of PAH contaminants, with preference for the more prevalent phenanthrene, from different origins having different chemical compositions, low cross-reactivity with unrelated compounds and is not significantly affected by normally found constituents of negative soil extracts, such as humic acid and fulvic acid.

Conventional hybridoma techniques are employed to prepare the anti-PAH monoclonal antibody (MAb) for the assay of the present invention, by the use of the immunogen reagent of the present invention. The method for producing MAbs is extremely powerful and allows for the preparation of a defined and reproducible Ab reagent. Hybridoma technology permits one to explore the entire b-cell repertoire of the immune system and to select unique antibody producing cells that produce antibodies having unique binding characteristics. The production of polyclonal antisera is much less controlled since polyclonal antisera contain numerous Ab populations each having varying specificity and sensitivity characteristics that are the products of numerous responding b-cell clones. MAb reagents are also homogeneous with a defined specificity, unlike polyclonal antisera which contain a mixed population of antibodies. Use and selection of hybridoma cell lines provides access MAb reagents that offer unique performance characteristics to the test system and consistency of the methods that utilize them.

A unique strategy is used for antibody production. This strategy involves developing an antibody to one or more specific structural elements that are present on a defined set of PAH compounds. The antibody is designed to recognize a defined pool of PAH compounds, having preference for phenanthrene. Recognition of a panel of compounds, instead of a single compound, allows the assay of the present invention to average out the concentration difference of any single component present in the differing PAH contaminants, while focusing on a prevalent indicator of PAH contamination, such as phenanthrene. Additionally, recognition of a collection of compounds rather than a single constituent contributes significantly to the sensitivity of the assay.

Preferably the pool of compounds selected for detection by the assay are predominantly the 3 and 4 ring polynuclear aromatic hydrocarbon compounds and a portion of the 5 and 6 ring polynuclear aromatic hydrocarbons. More preferably the compounds include the compounds acenaphthene, naphthalene, phenanthrene, anthracene, fluorene, benzo[a]anthracene, chrysene, fluoranthene, pyrene, benzo[b]fluoranthene, benzo[k]fluoranthene, benzo[a]pyrene and indeno(1,2,3-cd)pyrene, with a cross-reactivity with the monoclonal antibody of at least 9% for each of the PAH compounds. Even more preferably, the monoclonal antibody has cross-reactivity of at least 60% with the compounds phenanthrene, anthracene, fluorene, benzo[a]anthracene, chrysene and fluoranthene. Most preferably the monoclonal antibody has cross-reactivity of at least 100% with phenanthrene and anthracene. The immunogen of the present invention is used to immunize suitable hosts, such as mice.

Hosts responding to the immunization protocol are selected as splenocyte (or lymphoid cell) donors for hybridoma production. A culture of immune splenocytes in a defined tissue culture medium, such as HAT (hypoxanthine, aminopterine, thymidine), with conventional modified myeloma cells, capable of providing a hybridoma, provides the fusion products s-s, s-m, and m-m (with s=splenocyte and m=myeloma cell). Within tissue culture medium the s-s fusion product normally has a short lifetime and dies within days. Also, the m-m fusion product has a very short lifetime in the tissue culture medium used, lacking the metabolic components needed for DNA synthesis. However the s-m fusion product (or hybridoma) survives in tissue culture and retains the Ab-producing characteristics of the splenocyte parent, and the high rate of growth and relative immortality of the myeloma cell parent. This hybridoma cell line replicates itself readily in culture producing daughter cells that provide reproducible, homogeneous, and a consistent supply of the monoclonal anti-PAH antibody of the present invention.

The structure of the reporter molecule reagent can have a significant influence on immunoassay performance. Both the small molecule portion and the bridge structure of the derivative play an important role in antibody binding. Antibody and reagent pairs should be able to satisfy the following criteria:

Recognition and displacement by selected polynuclear aromatic hydrocarbon compounds in a sample Recognition and displacement and prerequisite sensitivity for PAH contaminants in a sample Low cross-reactivity to non-related compounds Approximately equal sensitivity for different types of PAH contaminants Insignificant negative soil matrix effects Antibody and reagent pairs which best satisfy the above criteria are most suitable for the assay of the present invention.

The immunoassay of the present invention is performed according to the following procedure. Monoclonal anti-PAH antibody is provided in an assay vessel, preferably immobilized in the assay vessel or other solid support, preferably to the bottom of a polystyrene tube, at a concentration, of from 0.005 to 20 $\mu$g/tube, preferably 0.1 to 0.4 $\mu$g/tube. The concentration and affinity of the antibody for the sample molecules and reporter reagent molecules directly influences the overall sensitivity of the final method. High, equivalent, affinity, and minimal non-specific signal generation, produces assays having superior sensitivity, with affinity binding constants, $K_a$, from $10^4$–$10^{12}$ L/mol, preferably $10^4$–$10^9$ L/mol.

The assay of the present invention compares a sample to be tested with a standard solution containing a compound cross-reactive with the antibody of the present invention, preferably phenanthrene, which is present in the standard solution in an amount sufficient to provide a 24 95% confidence level for detection at the desired level.

By way of example, the following describes a simultaneous test of a negative sample, a sample containing >100 ppm of PAHs, and a standard solution containing the equivalent of approximately 65 ppm of phenanthrene. Initially, following extraction from soil, the samples and standard are added to separate, and identical, antibody-coated test tubes. To each tube is added an equal volume of the reporter reagent solution. The tubes are then allowed to incubate at ambient conditions for approximately ten minutes.

During the incubation period sample molecules and reporter reagent molecules compete for the limited number of antibody binding sites that are available on the bottom of each of the tubes. The antibody concentration present is insufficient to permit the binding of all of the sample and reagent molecules simultaneously, and a situation somewhat analogous to the game of musical chairs exists, with the limited antibody binding capacity of the antibody molecules serving as the chairs in this example. The concentration of reporter reagent immobilized in each tube after incubation is inversely proportional to the concentration of PAHs in the sample or standard. The standard in the Standard tube limits the binding of the reporter reagent, the Negative sample permits more reporter reagent to bind (relative to the standard), and the positive sample permits less of the reporter reagent to bind (relative to the standard). At the end of the 10 minute incubation period, the tubes are washed leaving only the reagent that was retained by the immobilized antibody on the bottom of each tube.

The bound reagent/antibody complex remaining in each vessel or tube is next used to produce a detectable signal. Upon addition of a signal forming reagent(s), preferably a substrate/chromogen reagent pair, the enzyme molecule catalyzes the formation of a detectable signal. The signal that is generated is directly proportional to the concentration of reporter reagent present. A preferred substrate/chromogen reagent pair is $H_2O_2$ and tetramethyl-benzidine (TMB) which, when used with the preferred reporter reagent wherein the reporter molecule is the enzyme HRP (horseradish peroxidase), reacts with the enzyme portion of the reporter reagent, which facilitates the oxidation of TMB by $H_2O_2$ and generates a blue color.

Thus, the negative sample tube rapidly produces a solution that is visibly darker (i.e. greater absorbance) than the standard tube. The positive test sample produces a solution having less color (i.e. lower absorbance) than the standard tube. By comparing the signal of the sample tubes to the signal of the standard tube using a battery-operated comparative photometer, optionally included with the kit of the present invention, samples containing greater than or equal to the desired level of contamination can be detected with $\geq 95\%$ confidence. In this competitive ELISA method the final absorbance is inversely proportional to the ligand concentration present in the test sample.

The assay method of the present invention can process multiple samples in less than 30 minutes. The method is self-contained, field-compatible and does not require refrigeration or use hazardous components. The detection level can be set at the users discretion, for example by dilution of the sample extract, with 1 ppm as the maximum obtainable sensitivity obtainable using solid matrix samples and 30 ppb for aqueous samples.

The kit of the present invention contains four basic components: (1) a sample processing component for preparing the sample for testing by the assay method (described above), (2) at least one assay vessel, preferably a plurality, each containing an equivalent amount of an anti-PAH monoclonal antibody, preferably immobilized, (3) a standard solution containing the equivalent of 0.5–1.0 ppm (for soil) of a PAH compound in a suitable carrier, (4) a reporter reagent which is reconstituted to form a solution containing a reporter reagent which is cross-reactive with the monoclonal anti-PAH antibody, in a suitable carrier, where the reporter reagent is preferably a lyophilized enzyme-conjugate reagent, and (5) means for forming and detecting a signal indicating the presence or absence of PAH contamination in the sample being tested. Optionally, the kit contains one or more of the following additional components: (6) wash solutions for performing the wash step of the assay method, (7) weighing boats into which the sample is weighed using (8) a battery-operated scale, (9) one or more filters for preparing a clarified leachate sample, (10) one or more dilution vials, (11) substrate solution and (12) stop solution to halt signal formation by the signal-forming reagent. Preferably the assay is provided in a coated-tube format in which the means for forming and detecting a signal comprises the use of a substrate/chromogen reagent pair which forms a detectable colored signal with the level of PAH contamination determined by comparison of the color developed by the test samples to the color of the kit standard.

In order to eliminate temperature variations, timing errors and operator mistakes, the standard is preferably run in parallel with the samples. Therefore, any assay variations will equally affect both the standard and the samples. Using this format with the standard run in parallel, the assay has the following characteristics:

1. The sensitivity in solid samples is 1 ppm of PAH at $\geq 95\%$ confidence level.
2. Different soil matrices cause little interference in the assay.
3. The test is reproducible from lot-to-lot, day-to-day, and person-to-person.
4. The assay is operable over a temperature range of 4°–37° C., preferably 15°–37° C.
5. Storage at room temperature (up to 30° C.) is acceptable.

The immunoassay of the present invention has many advantages, including field screening compatibility, speed in obtaining a result, and a lack of false negative results. Specific characteristics had to be integrated into the method in order to achieve these advantages. The first was to minimize the incidence of false negative results. A false negative test does not detect a contaminated sample at the concentration of interest and therefore, can be potentially dangerous both to the customer and the environment. A false positive, on the other hand, might be inconvenient but not dangerous. Therefore, the immunoassay of the present invention was designed to detect positive solid matrix samples containing $>1$ ppm of PAHs with a minimum of false negative results. This is accomplished by using a standard containing the equivalent of phenanthrene in soil at 0.65 ppm to detect 1 ppm PAHs with a $\geq 95\%$ confidence level. Preferably, two standards are run with each assay to minimize false negative results and to provide an internal quality control parameter indicating the competency of the operator and the integrity of the chemistry.

The immunoassay has also been simplified by making it a semiquantitative test using a standard at a single concentration. The use of one standard concentration greatly simplifies the test protocol and eliminates the data manipulation and expensive instrumentation that are normally necessary for quantitative tests. The test becomes a semiquantitative "yes/no" test that determines whether a soil sample contains greater or less than a target level of PAH contamination. The use of multiple standards at varying concentrations could be used to allow one to perform a quantitative assay by interpolation of sample signal from the signal of a standard curve.

The immunoassay of the present invention makes possible the rapid screening of numerous samples in the field for PAHs. The rapid, on-site screening of multiple samples is a significant advantage compared to the standard analytical GC or HPLC methods. The quick screening of samples allows quick answers to important questions concerning the project, such as, has the plume of contaminated soil been located, has the area been remediated to acceptable levels, and does additional soil need to be removed? With the immunoassay method of the present invention, personnel, time and equipment can be used more cost-effectively.

Having generally described this invention, a further understanding can be obtained by reference to certain specific examples which are provided herein for purposes of illustration only and are not intended to be limiting unless otherwise specified.

EXAMPLES

Example 1: Preparation of Assay components
Preparation of Monoclonal Antibody

Female Balb/c mice received a primary subcutaneous immunization with 50 ug of β-methylnaphthalene derivatized to bovine serum albumin in adjuvant (MPL+TDM Emulsion, RIBI Immunochem Research, Inc., Hamilton, Mont.). Subcutaneous secondary injections (25 ug) were given at day 21, 35, and then monthly. The production of monoclonal antibodies was performed according to conventional procedures (see Milstein, Cancer, 49:1953–1957 (1982)). Hybridoma cultures producing monoclonal antibodies recognizing free hapten by EIA were cloned by limiting dilution. Clone F35-2Z11 was selected based upon specificity, and interference criteria.

Horseradish Peroxidase Conjugate Reagent

Horseradish peroxidase (HRP) conjugate reagent was prepared with a hydrazide derivative of naphthalene using the conventional periodate method (see Nakane et al *J. Histochem. Cytochem.* 22:1084 (1971)).

Antibody Coated Tubes

Antibody coated tubes were prepared by passively coating polystyrene (12×75 mm, NUNC) tubes with the monoclonal F12-3C8 antibody diluted in PBS and incubating overnight. The NUNC polystyrene tubes were rinsed with hexane prior to use and were all from the same lot.

Example 2: PAH Immunoassay Procedure —1 ppm in soil

The immunoassay method of the present invention has been demonstrated as follows:

10 g of a soil sample were placed in an extraction vial containing 20 mL of methanol and 5 steel pellets (6mm) and the vial and its contents shaken for 1 minute to disperse the soil particles and extract the PAHs. The sample was then filtered to clarify the sample extract using a glass fiber depth filter and a 0.45 μ Teflon filter. 45 uL of the clarified filtrate sample was mixed with 955 μl of 10mM PBS (pH=7.4) and the resulting mixture added to lyophilized enzyme conjugate reagent (0.3 μg) and mixed. At the same time, 2×45 uL of the phenanthrene standard are similarly treated. The sample and the two standards were then poured into three identical antibody coated tubes, respectively, and the resulting solution mixed. The resulting solution was incubated for 10 minutes at ambient temperature and then washed 4× with a wash buffer (detergent-saline solution). 250 uL of tetramethylbenzidene solution (KP Laboratories, Cat. No. 50-76-02) was added along with 250 uL of hydrogen peroxide solution (KPL, Cat. No. 50-65-02) and the resultant solution mixed. After incubating for 2.5 minutes the color development reaction was stopped with 250 uL of stop solution (1M sulfuric acid).

The optical density (OD) of the test sample was compared to the OD of the phenanthrene standard (0.65 ppm soil equivalents) which was tested simultaneously with the sample. If the sample OD is less than the standard OD, the sample contains more than 1 ppm PAH. If the sample OD is greater than the standard OD, the sample contains less than 1 ppm PAH. Other concentration ranges can be assessed by diluting the test samples with suitable diluents, as long as they are non-reactive with the components of the assay.

To achieve the goal of $\geq 95\%$ confidence of phenanthrene detection at 1 ppm, the concentration of the phenanthrene standard was determined by using a statistical approach. The standard was set at a point where the mean of the standard absorbance minus 2 standard deviations (SD) does not overlap the mean of the signal at 1 ppm. The other requirement is that the standard OD plus 2 SD must not overlap with the range of a panel of interfering negative soils. Using this method, the standard was established to be 0.65 ppm (soil equivalents) (Table II). A dilution of the sample is used to reduce interference from methanol and to test at varying target concentrations. A 1 ppm phenanthrene sample thus yields a positive interpretation, relative to the 0.65 ppm kit standard, with $\geq 95\%$ confidence Sensitivity profiles were prepared as a measurement of assay performance using phenanthrene spikes compared to the kit standard. These profiles serve three purposes in the validation process. First, they indicate whether the kit standard is set appropriately. Second, the profiles help establish and support the sensitivity claims with $\geq 95\%$ confidence. Third, they are used to evaluate matrix effects and assay variability due to lot, operator and temperature differences.

Figure 1:
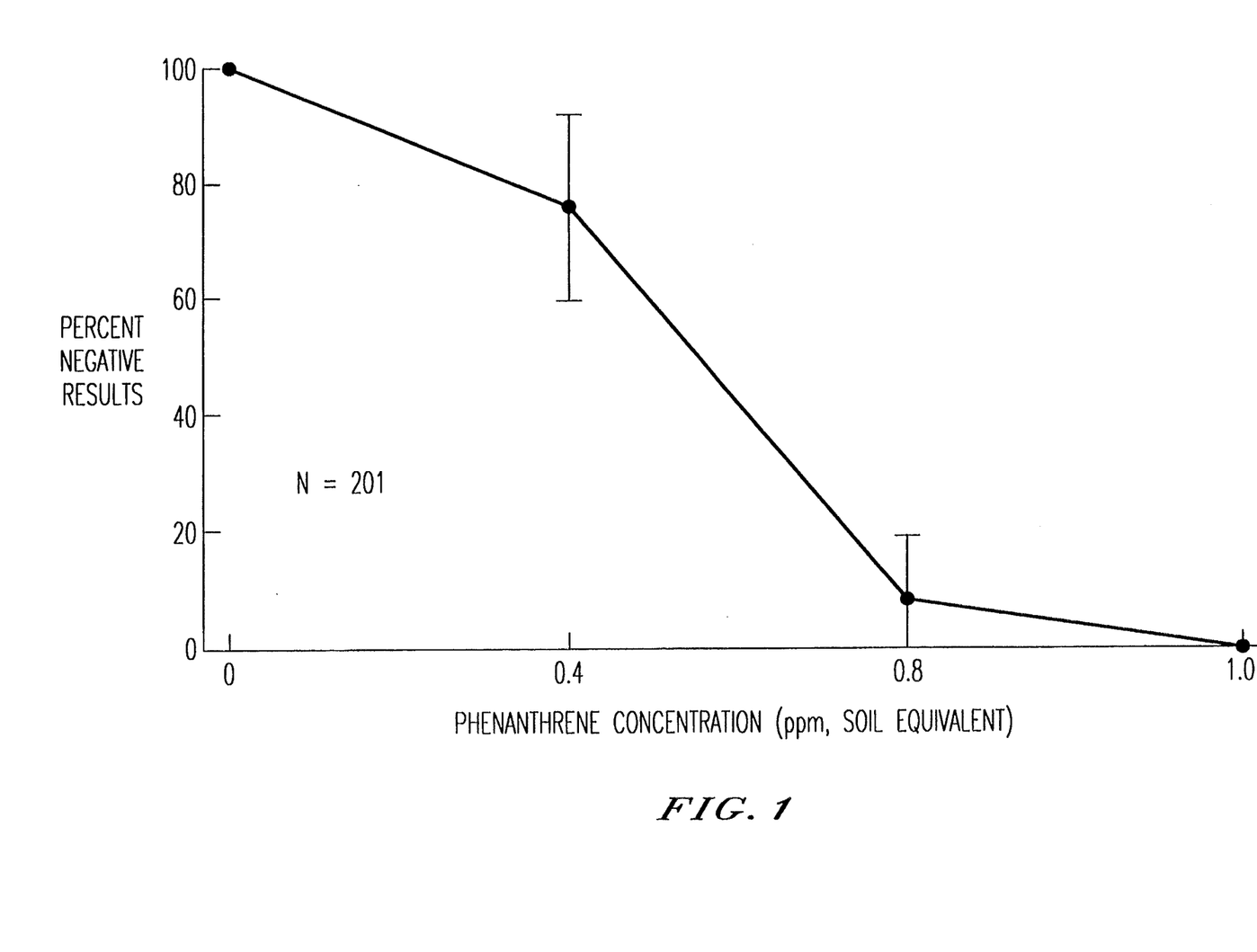
FIG. 1 displays the sensitivity profiles of 201 observations assayed at room temperature across four validation lots, twelve matrices and 3 operators, using the PAH immunoassay of the present invention.

FIG. 1 displays the sensitivity profiles of 201 observations assayed at room temperature across four validation lots, twelve matrices and 3 operators. This figure demonstrates that the standard (0.65 ppm soil equivalents) is set appropriately since it gave correct results for each phenanthrene sample having concentration at 0.4 and 0.8 ppm. Furthermore, FIG. 1 illustrates a $\geq 95\%$ confidence level in negative results at 0 ppm and in positive results at $\geq 1$ ppm.

The effect of soil matrices is an important determinant in setting the kit standard. Confirmed negative soils representing a variety of soil types from different geographical locations were used to evaluate matrix effect. The first approach to evaluating matrix effects was to spike soil extracts with 1 ppm phenanthrene and compare the $B_{1ppm}$ signal (soil) to the Bo signal obtained with methanol. The results, listed in Table II, indicate that the range of this ratio was 0.40 to 0.54. Therefore, there is minimal soil effect on signal generated in the presence of phenanthrene.

Further evaluation of matrix effect was accomplished by running sensitivity profiles in which phenanthrene levels were spiked into soil extracts and compared to the kit standard. All matrices showed a consistent cross-over between positive and negative results with insignificant difference in the number of false results.

TABLE II

Soil Matrix Effect on Bo and Standard Signal

| Soils | Bo soil / Bo MeOH | | Bstd soil / Bo MeOH |
|---|---|---|---|
| MeOH | 1.00 | | 0.48 |
| EnSys | 1.00 | | 0.54 |
| Florida | 0.94 | | 0.51 |
| Loam | 0.92 | | 0.47 |
| Ohio | 0.93 | | 0.47 |
| Sandy Clay | 0.96 | | 0.49 |
| Sandy Loam | 0.99 | | 0.47 |
| Silty Clay | 0.90 | | 0.48 |
| Silty Loam | 0.86 | | 0.40 |
| Wake | 0.89 | | 0.48 |
| Wilkesboro | 0.94 | | 0.48 |
| Texas | 1.00 | | 0.53 |
| ERA | 1.04 | | 0.50 |
| Average | 0.95 | Average | 0.49 |
| −2 SD | 0.85 | +2 SD | 0.56 |
| (Soil equivalent) | 300 ppb | (Soil equivalent) | 650 ppb |

SPECIFICITY

The matrix effect of 12 soils was determined by comparing the Bo(soil) signal at a 1:68.7 dilution to the Bo(methanol) signal. The results in Table II present the ratio of Bo(soil) to Bo(methanol) for each soil. With no matrix effect the ratio of Bo(soil) to Bo(methanol) equals 1.0. Most of the soils do not significantly differ from the Bo(methanol) signal, with the average ratio=0.95.

CROSS-REACTIVITY

A. Specificity with Method 8310 EPA PAHs

Cross-reactivity of PAHs detected by the EPA Method 8310 were tested using the method of the present invention. The results are outlined in Table III.

The results presented in Table III demonstrate that the 3- and 4-ringed PAHs are recognized in the PAH immunoassay of the present invention at a very sensitive level of ≧8.1 ppm. In spite of solubility issues associated with the larger 5- and 6-ring PAHs, most of these structures are also recognized at low levels in the immunoassay with the exception of dibenzo(a,h)anthracene and benzo(ghi)perylene. These results suggest that the test is a good screening method for total PAH levels.

The most interesting carcinogenic PAH from a market perspective is benzo(a)pyrene. If this compound is present in soils at concentrations of ≧8.3 ppm the PAH immunoassay of the present invention will provide a positive result.

B. Specificity with Other Potentially Cross-Reactive Compounds

Polynuclear aromatic hydrocarbons not detected in the EPA 8310 Method were also evaluated for cross-reactivity in the PAH assay of the present invention. In addition other potentially cross-reactive compounds were tested. The results are summarized in Table IV.

Chlorinated and methylated naphthalenes are frequently found at high levels at gas manufacturing plants. A high contamination of the naphthalene derivatives would give a positive interpretation of total PAHs.

The single ring compounds tested, such as benzene and phenol, were not detected in the immunoassay at 200 ppm levels. These results demonstrate that many non-PAH compounds commonly found at wood-treating sites and gas manufacturing sites are not cross-reactive in the assay and will not affect the rate of false positive results except when they are present in excessively high concentrations.

These results demonstrate that the assay is highly sensitive and specific for polynuclear aromatic hydrocarbon compounds and has little cross-reactivity toward other compounds.

TABLE III

Cross-Reactivity of Method 8310 EPA PAHs

| Compound | Concentration Giving A Positive Result; (ppm, soil equivalent) | Percent Cross-Reactivity |
|---|---|---|
| 2 Rings | | |
| Naphthalene | 200 | 0.5% |
| 3 Rings | | |
| Acenaphthene | 8.1 | 12% |
| Acenaphthylene | 7.5 | 13% |
| Phenanthrene | 1.0 | 100% |
| Anthracene | 0.81 | 123% |
| Fluorene | 1.5 | 67% |
| 4 Rings | | |
| Benzo(a)anthracene | 1.6 | 64% |
| Chrysene | 1.2 | 84% |
| Fluoranthene | 1.4 | 73% |
| Pyrene | 3.5 | 29% |
| 5 Rings | | |
| Benzo(b)fluoranthene | 4.6 | 22% |
| Benzo(k)fluoranthene | 9.4 | 11% |
| Benzo(a)pyrene | 8.3 | 12% |
| Dibenzo(a,h)anthracene | >200 | <0.5% |
| 6 Rings | | |
| Indeno(1,2,3-cd)pyrene | 11 | 9.4% |
| Benzo(ghi)perylene | >200 | <0.5% |

TABLE IV

Cross-Reactivity of Non-EPA PAHs and Other Compounds

| Compound | Concentration Giving a Positive Result; (ppm, soil equivalent) | Percent Cross-Reactivity |
|---|---|---|
| Non-EPA PAHs | | |
| 1-methylnaphthalene | 54 | 1.8% |
| 2-methylnaphthalene | 58 | 1.7% |
| 1-chloronaphthalene | 59 | 1.7% |
| Halowax 1013 | 18 | 5.7% |
| Halowax 1051 | >200 | <0.5% |
| Dibenzofuran | 14 | 7.2% |
| Other Compounds | | |
| Benzene | >200 | <0.5% |
| Toluene | >200 | <0.5% |
| CCA | >200 | <0.5% |
| Phenol | >200 | <0.5% |
| Creosote | 5.4 | 18.5% |
| 2,4,6-Trichlorobenzene | >200 | <0.5% |
| 2,3,5,6-Tetrachlorobenzene | >200 | <0.5% |
| Pentachlorobenzene | >200 | <0.5% |
| Pentachlorophenol | >200 | <0.5% |
| Bis(2-ethylhexyl) phthalate | >200 | <0.5% |
| Aroclor 1254 | >200 | <0.5% |
| Aroclor 1260 | >200 | <0.5% |

OPERATING TEMPERATURE RANGE

Establishing the temperature range for the operation of the PAH assay of the present invention is necessary for its usefulness as a field test kit. Ideally, the test should perform at 4° C. to 37° C. In order to evaluate performance at different temperatures, sensitivity profiles were analyzed for reproducibility (OD difference between standards), absolute OD value (percent change in Bo signal compared to the mean room temperature signal) and interpretation of positive and negative results. The results of the experiments are listed in Table V.

TABLE V

| Temperature | Assay Performance at Various Temperatures | | | | |
|---|---|---|---|---|---|
| | False Positive 0 ppm | False Negative 1 ppm | Standard Delta mean | Standard Delta std dev | Mean Bo Signal Change from RT |
| 4° C. (11° F.) | 1/30 | 0/27 | 0.07 | 0.05 | −37% |
| 32° C. (90° F.) | 0/40 | 2/42 | 0.05 | 0.05 | −41% |
| 38° C. (100° F.) | 2/18 | 4/18 | 0.05 | 0.04 | −38% |

The PAH assay of the present invention can be operated at temperatures between 4° C. and 32° C. with ≧95% confidence in results at the 0 ppm and 1 ppm phenanthrene levels. An increase in the frequency of false positive and false negative results was observed at 36° C. The differences between the standard pairs was not affected by the operating temperature (compare to Table V) which demonstrates that the temperature extremes did not affect the assay precision. Interestingly, the Bo signal was suppressed at either high or low temperatures without affecting the assay interpretation. In conclusion, the preferred operating range for the PAH test of the present invention is 4° C. to 32° C.

TEST KIT STABILITY

The test kit of the present invention, containing the immunoassay components of the present invention, has been found to be stable for extended periods of time. Projections indicate a shelf life at 37° C. of ≧1 year.

The advantages of immunoassay technology can be attributed to the underlying lock and key binding principle and its compatibility with aqueous matrixes. This method does not require the chromatographic separation of sample components, nor does it require that compounds absorb visible, infrared or UV for detection. Interferences from other compounds are considerably less of a problem because of the conformational nature of the antibody binding process. Sample processing time is significantly reduced, and the direct testing of aqueous samples, or water-compatible leachates of soil, can be performed. The technology offers a unique, and conservative, approach to field screening. The incidence of false negative data is exceptionally low. Aspects that tend to interfere with immunoassay methods of this type tend to cause an overestimation of contamination, or false positive result by minimizing the binding of enzyme conjugate reporter molecule to antibody or suppressing signal generation by the enzyme.

This method offers significant versatility and performance advantages. It is a convenient and effective new tool that can enhance the efficiency of site management activities and the utilization of our national laboratory system.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. An immunoassay for determining the presence of PAHs in a sample, comprising:

(A) combining (ia) a monoclonal antibody with specific reactivity towards phenanthrene, anthracene, fluorene, benzo(a)anthracene, chrysene, and fluoranthene, obtained by (i) producing an immune response in a vertebrate host by immunization with an immunogen comprised of a derivative. moiety of the formula Ar—X—(CH$_2$)$_n$—Y—Z wherein Ar is a naphthyl group having one or more substitents selected from the group consisting of H, CH$_3$ and CH$_2$CH$_3$; X is a single bond, Y is $$-\overset{O}{\underset{\|}{C}}-NH-, \quad -NH-\overset{O}{\underset{\|}{C}}-, \quad -CH_2\overset{O}{\underset{\|}{C}}-NH-, \text{ or}$$

$$-NR^1-;$$

wherein R$^1$ is selected from the group consisting of H, C$_1$-C$_2$ alkyls, and linear, branched and cyclic C$_3$-C$_6$ alkyls; n is 0 or an integer from 1 to 4; linked to an immunogen carrier molecule Z;

(ii) preparing a hybridoma from the lymphoid cells said host;

(iii) selecting said hybridoma which produces said monoclonal antibody: and (iv) obtaining said monoclonal antibody from said hybridoma, with (ib) a mixture of the sample and a reporter molecule reagent which is cross reactive with said monoclonal antibody, wherein said reporter molecule reagent is susceptible to producing a detectable signal, to form an assay mixture;

(B) incubating said assay mixture to allow competitive monoclonal antibody binding between at least one of said plurality of characteristic compounds, if present, in the sample, and said reagent;

(C) causing production of said signal and correlating said signal to the amount of reagent bound to said monoclonal antibody to obtain a measure of the amount of PAHs in said sample.

2. The immunoassay of claim 1, wherein said monoclonal antibody is an immobilized monoclonal antibody.

3. The immunoassay of claim 1, wherein said monoclonal antibody is not immobilized.

4. The immunoassay of claim 1, wherein said reporter molecule reagent has the formula Ar—X—(CH$_2$)$_n$—Y—(REPORTER MOIETY)

wherein Ar is an aromatic benzenoid hydrocarbon group having from 2 to 6 benzenoid rings, each ring of which may be substituted by one or more substituents selected from the group consisting of H, CH$_3$ and CH$_2$CH$_3$; X and Y are each, independently $$-\overset{O}{\underset{\|}{C}}-NH-, \quad -NH-\overset{O}{\underset{\|}{C}}-, \quad -CH_2\overset{O}{\underset{\|}{C}}-NH-, \quad -\overset{O}{\underset{\|}{C}}-,$$

$$-O-CH_2-CO-NH-NH-, \quad -NR^9-, \quad -S-$$

or —O—;

or X is

—COO—, or a single bond wherein $R^9$ is selected from the group consisting of H, $C_1$-$C_2$ alkyls, and linear, branched and cyclic $C_3$-$C_6$ alkyls; and n is 0 or an integer from 1 to 4.

5. The immunoassay of claim 4, wherein said reporter moiety is an enzyme selected from the group consisting of horseradish peroxidase, alkaline phosphatase, β-galactosidase, glucose oxidase, G6-PDH and urease.

6. The immunoassay of claim 5, wherein said enzyme is horseradish peroxidase.

7. The immunoassay of claim 1, further comprising simultaneously assaying a standard solution containing at least one member selected from the group of phenanthrene, anthracene, fluorene, benzo[a]anthracene, chrysene, and fluoranthene, and said sample.

8. The immunoassay of claim 1, further comprising a step of processing the sample prior to step (A) by extracting the sample to obtain an extract containing said PAHs, if present, and filtering said extract to provide a clarified extract for use as the sample in steps (A)–(C).

9. A monoclonal antibody having specific reactivity towards phenanthrene, anthracene, fluorene, benzo(a)anthracene, chrysene, and fluoranthene, obtained by (i) producinq an immune response in a vertebrate host by immunization with an immunogen comprised of a derivative moiety of the formula Ar—X—(CH₂)ₙ—Y—Z wherein Ar is a naphthyl group having one or more substituents selected from the group consisting of H, $CH_3$ and $CH_2CH_3$; X is a single bond, Y is wherein $R^1$ is selected from the group consisting of H, $C_1$-$C_2$ alkyls, and linear, branched and cyclic $C_3$-$C_6$ alkyls;

n is 0 or an integer from 1 to 4; linked to an immunogen carrier molecule Z;

(ii) preparing a hybridoma from the lymphoid cells of said host;

(iii) selecting said hybridoma which produces said monoclonal antibody; and (iv) obtaining said monoclonal antibody from said hybridoma.

10. The monoclonal antibody of claim 9, having a further specific reactivity for acenaphthene, naphthalene, pyrene, benzo[b]fluoranthene, benzo[k]fluoranthene, benzo[a]pyrene and indeno(1,2,3-cd)pyrene.

11. The monoclonal antibody of claim 9, wherein said specific reactivity is a cross-reactivity of at least 60%.

12. The monoclonal antibody of claim 10, wherein said further specific reactivity is a cross-reactivity of at least 9%.

13. The monoclonal antibody of claim 9, wherein said specific reactivity is a cross-reactivity of at least 60% wherein said cross-reactivity with phenanthrene and anthracene is at least 100%.

14. An immunoassay kit useful for detecting the presence of PAHs in a sample, said kit comprising:

(i) a reaction vessel means containing an immobilized monoclonal antibody having specific reactivity towards phenanthrene, anthracene, fluorene, benzo(a)anthracene, chrysene, and fluoranthene, wherein said monoclonal antibody is obtained by (a) producing an imune response in a vertebrate host by immunization with an immunogen comprised of a derivative moiety of the formula Ar—X—(CH₂)ₙ—Y—Z wherein Ar is a naphthyl group having one or more substituents selected from the group consisting of H, $CH_3$ and $CH_2CH_3$; X is a single bond, Y is wherein $R^1$ is selected from the group consisting of H, $C_1$-$C_2$ alkyls, and linear, branched and cyclic $C_3$, $C_6$ alkyls; n is 0 or an integer from 1 to 4; linked to an immunogen carrier molecule Z;

(b) preparinqa hybridoma from the lymphoid cells of said host;

(c) selecting said hybridoma which produces said monoclonal antibody; and (d) obtaining said monoclonal antibody from said hybridoma;

(ii) a standard solution comprising at least one PAH compound selected from the group consisting of phenanthrene, anthracene, fluorene, benzo(a)anthracene, chrysene, and fluoranthene, and a carrier;

(iii) a reporter molecule reagent, which is cross-reactive with said monoclonal antibody; and (iv) means for causing said reporter moiety to generate a signal and means for detecting said signal.

15. The kit of claim 14, wherein said standard solution comprises from 0.5 to 200 ppm (soil equivalents) of said compound.

16. The kit of claim 14, wherein said reporter molecule reagent is a compound of the formula Ar—X—(CH₂)ₙ—Y—(REPORTER MOIETY)

wherein Ar is an aromatic benzenoid hydrocarbon group having from 2 to 6 benzenoid rings, each ring of which may be substituted by one or more substituents selected from the group consisting of H, $CH_3$ and $CH_2CH_3$; X and Y are each, independently or X is —COO—, or a single bond wherein $R^9$ is selected from the group consisting of H, $C_1$–$C_2$ alkyls, and linear, branched and cyclic $C_3$–$C_6$ alkyls; and n is 0 or an integer from 1 to 4.

17. The kit of claim 16, wherein said reporter moiety is an enzyme selected from the group consisting of horseradish peroxidase, alkaline phosphatase, β-galactosidase, glucose oxidase, G6-PDH and urease.

18. The kit of claim 17, wherein said enzyme is horseradish peroxidase.

19. The kit of claim 14, wherein said reaction vessel means is a plurality of vessels, each containing an equivalent amount of said monoclonal antibody.

20. The kit of claim 14, wherein said reporter molecule reagent is a lyophilized reporter molecule reagent which is reconstituted prior to use.

21. The kit of claim 14, further comprising a sample processing means for preparing the sample for testing.

22. The kit of claim 21, wherein said sample processing means comprises a weighing means, a dispersion vessel, an extraction solvent, dispersing pellets, and a filtration means.

* * * * *